United States Patent [19]

Rohlfs et al.

[11] 4,337,214

[45] Jun. 29, 1982

[54] N-(HYDROXY METHYL)-1-AMINO ALKANE-1,1-DIPHOSPHONIC ACIDS, PROCESS OF MAKING SAME, AND COMPOSITION FOR AND METHOD OF USING SAME AS STABILIZING AGENTS IN PEROXIDE-CONTAINING BLEACHING BATHS

[75] Inventors: Hans-Adolf Rohlfs, Heidelberg; Alfred Kling, Ladenburg; Guenter Raab, Laudenbach; Michael Vogt, Moerlenbach; Viktor Specht, Dossenheim; Ulrike Schaetzke, Weinheim-Sulzbach, all of Fed. Rep. of Germany

[73] Assignee: Benckiser-Knapsack GmbH, Ladenburg, Fed. Rep. of Germany

[21] Appl. No.: 177,885

[22] Filed: Aug. 14, 1980

[30] Foreign Application Priority Data

Aug. 22, 1979 [DE] Fed. Rep. of Germany ....... 2933969

[51] Int. Cl.³ .............................................. C07F 9/38
[52] U.S. Cl. ................................... 260/502.5; 8/111; 252/186.22; 252/186.29
[58] Field of Search ...................................... 260/502.5

[56] References Cited

U.S. PATENT DOCUMENTS 3,422,139 1/1969 Talet et al. ........................... 562/567
3,860,391 1/1975 Kling et al. ............................... 8/111
4,029,696 6/1977 Sommer et al. ................... 260/502.5
4,100,067 7/1978 Sommer et al. ........................ 210/58

FOREIGN PATENT DOCUMENTS 568570 1/1959 Canada ............................... 562/567
2504724 8/1976 Fed. Rep. of Germany .

Primary Examiner—Joseph E. Evans
Attorney, Agent, or Firm—Schwartz, Jeffery, Schwaab, Mack, Blumenthal & Koch

[57] ABSTRACT

Disclosed are novel N-(hydroxy methyl)-1-amino alkane-1,1-diphosphonic acids and N,N-Bis-(hydroxymethyl)-1-amino alkane-1,1-diphosphonic acids, preferably N-(hydroxy methyl)-1-amino ethane-1,1-diphosphonic acid, N,N-Bis-(hydroxy methyl)-1-amino ethane-1,1-diphosphonic acid, and their water-soluble salts. Also disclosed is a method for preparing these compounds by reacting the corresponding 1-amino alkane-1,1-diphosphonic acids with formaldehyde in an alkaline medium at elevated temperature. The new phosphonic acid compounds are excellent stabilizing agents for hydrogen peroxide-containing alkaline bleaching liquors, especially useful for bleaching cellulose fibers and blends thereof with synthetic fibers, such as polyester fibers.

3 Claims, 5 Drawing Figures

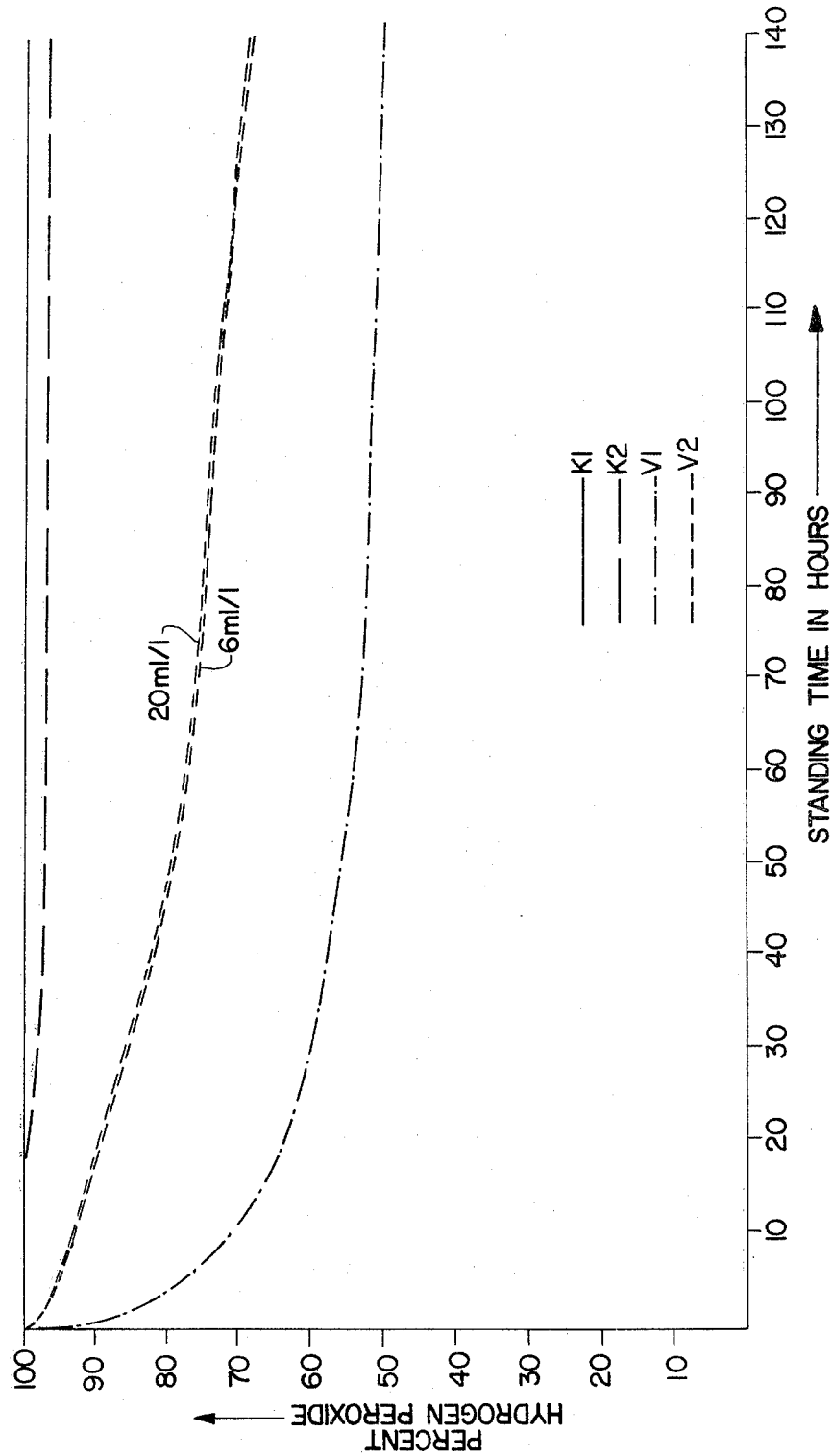

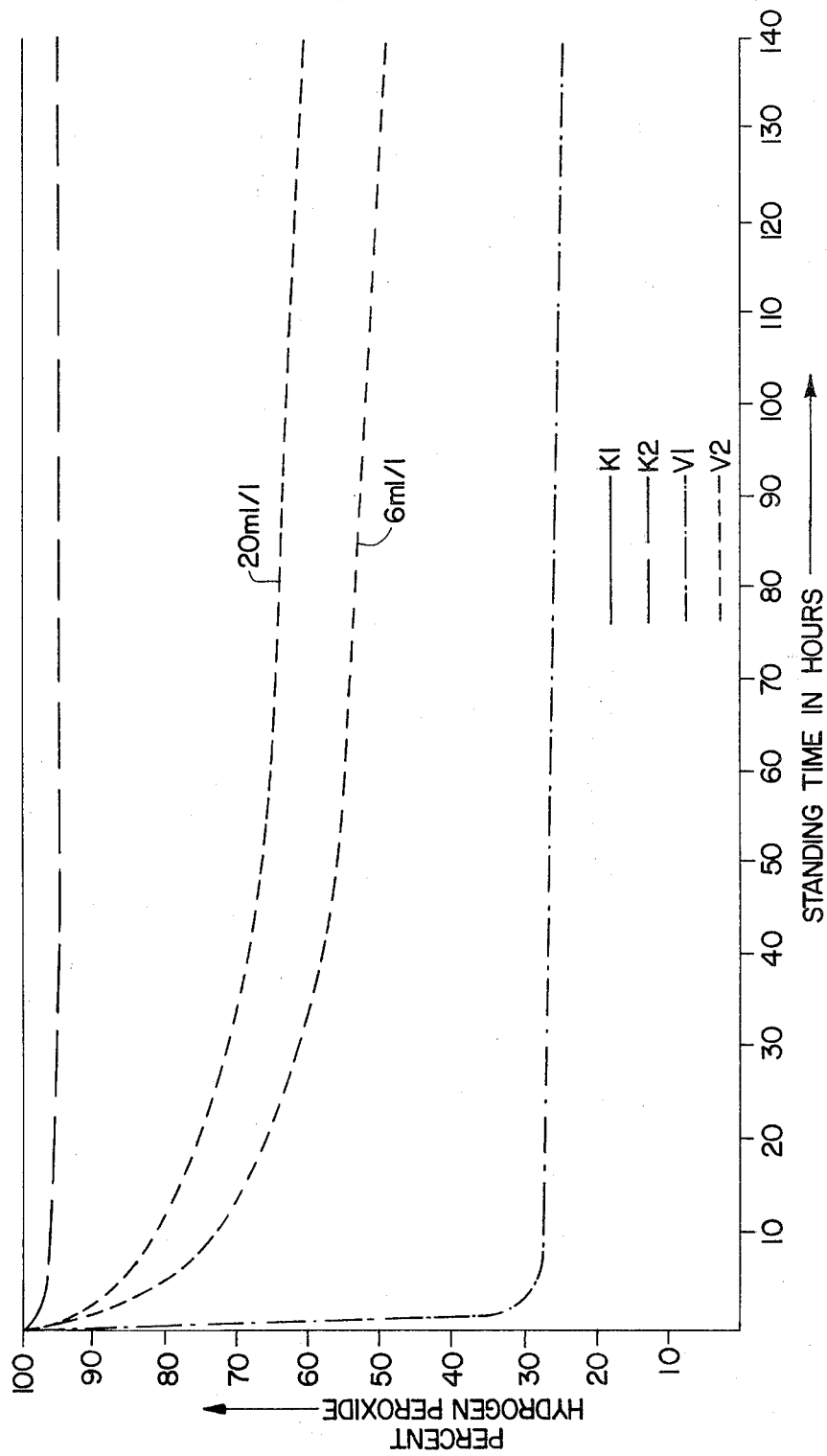

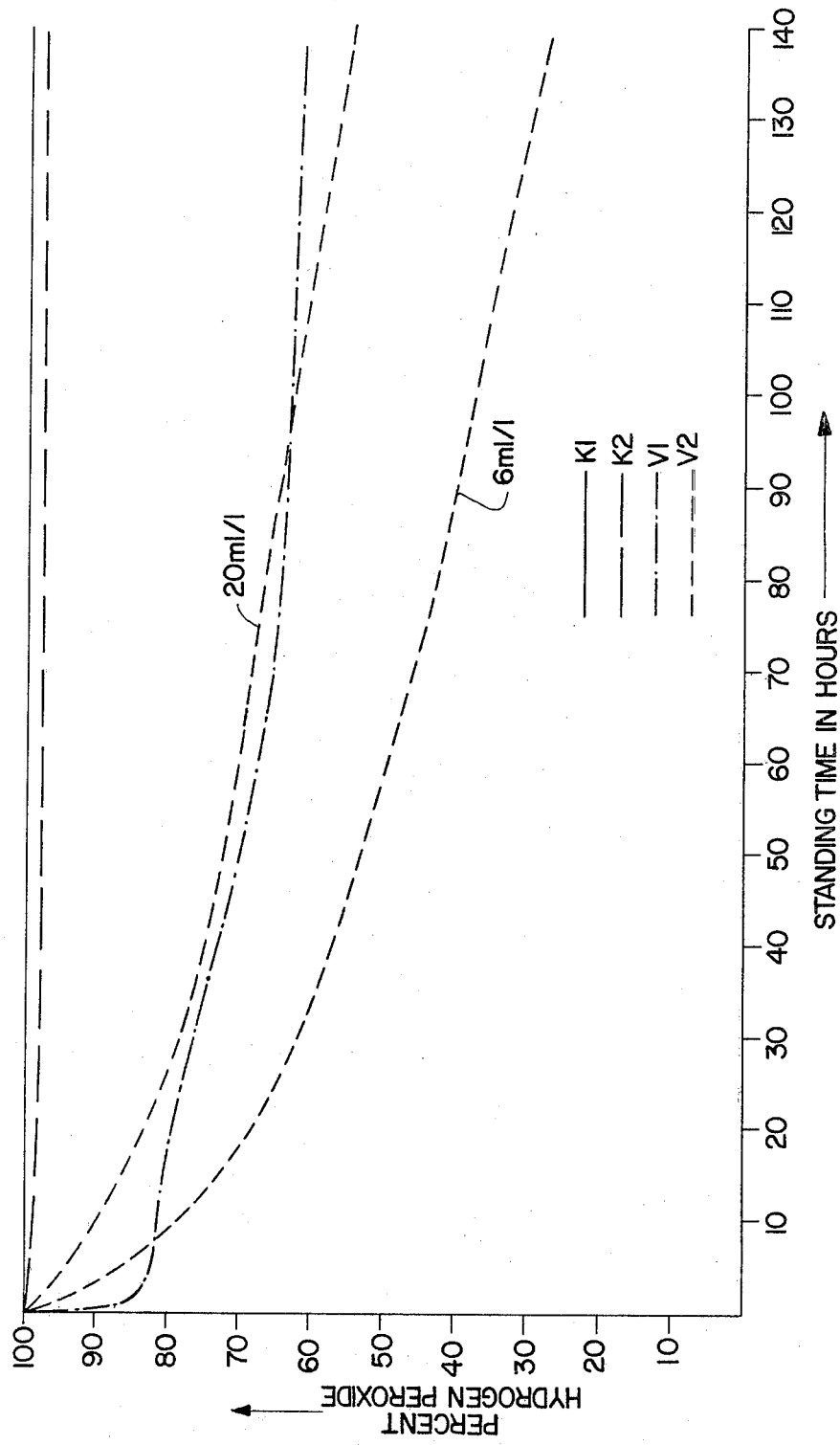

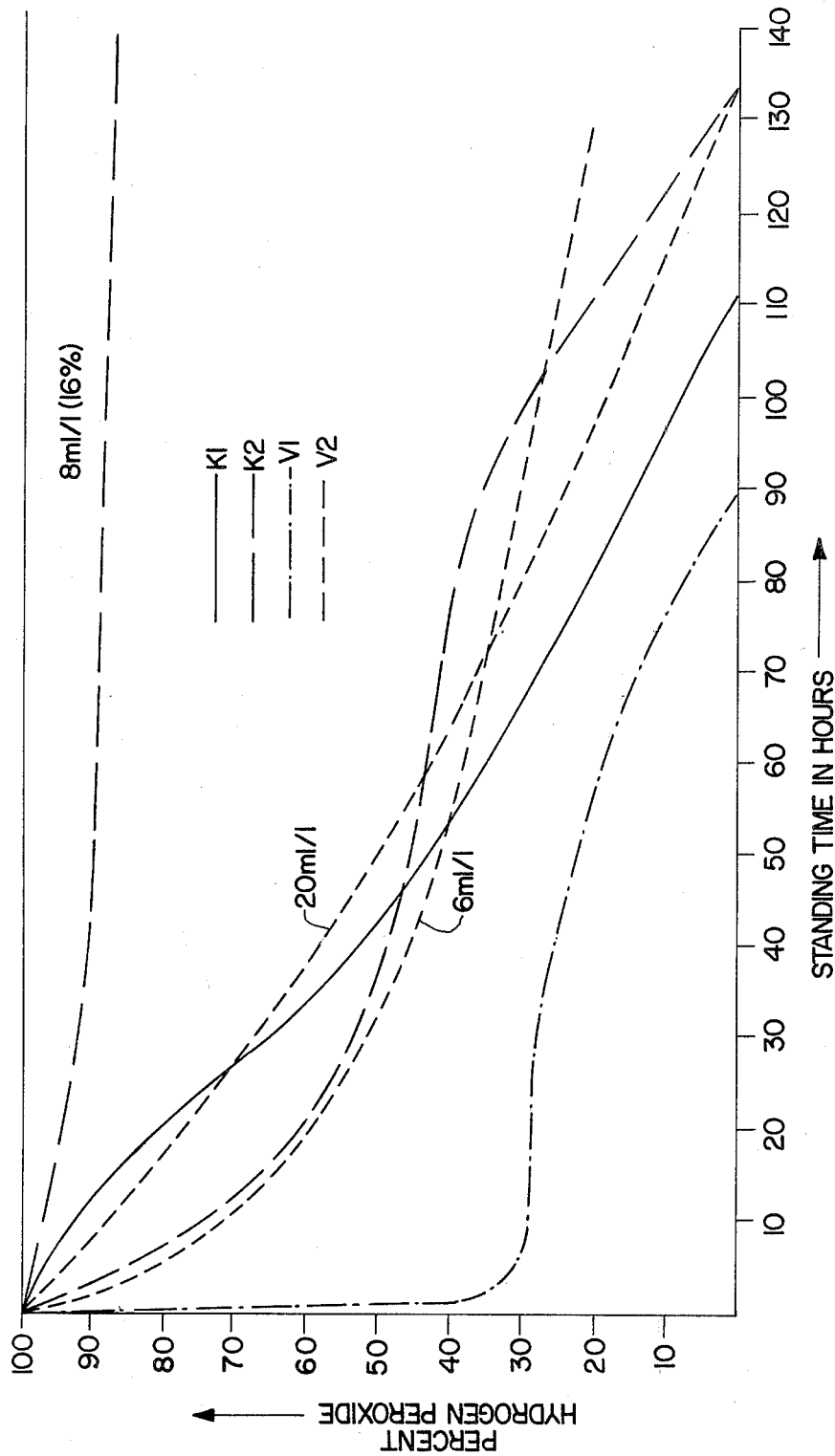

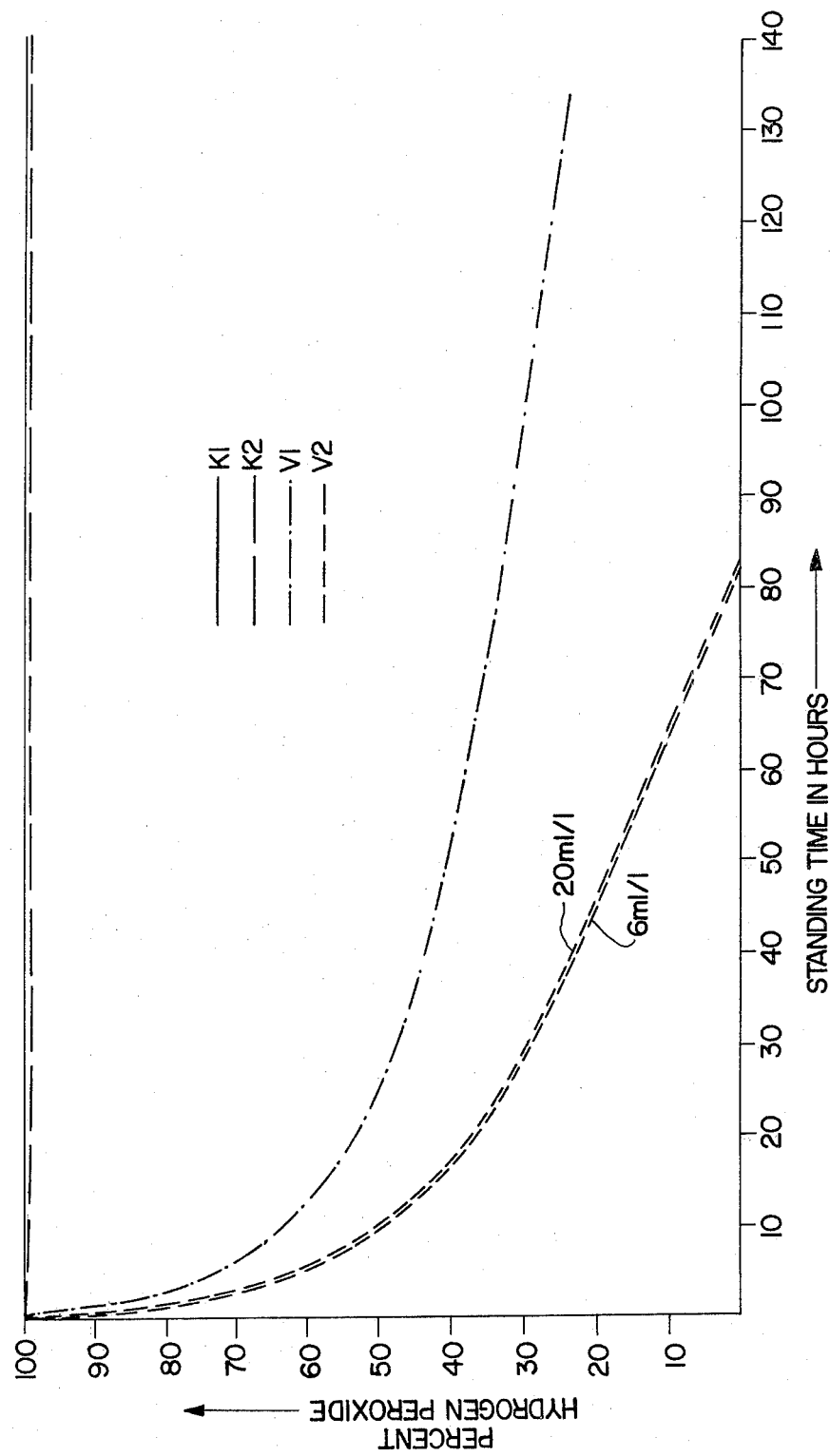

N-(HYDROXY METHYL)-1-AMINO ALKANE-1,1-DIPHOSPHONIC ACIDS, PROCESS OF MAKING SAME, AND COMPOSITION FOR AND METHOD OF USING SAME AS STABILIZING AGENTS IN PEROXIDE-CONTAINING BLEACHING BATHS

BACKGROUND OF THE INVENTION

1. Field of the Invention

The present invention relates to novel and useful amino alkane phosphonic acid compounds and more particularly to novel N-(hydroxy methyl) amino alkane phosphonic acids and their salts, to a process of producing such phosphonic acid compounds, to methods of using such compounds as stabilizing agents in perioxide-containing bleaching baths and especially to methods for bleaching cellulose fibers, either alone or in a blend with synthetic fibers, at a pH-value of at least 9.0, and to compositions containing such amino alkane phosphonic acid compounds.

2. Description of the Prior Art

N-(hydroxy alkyl) amino alkane-1,1-diphosphonic acids in which one or two hydrogen atoms at the nitrogen atoms are substituted by hydroxy alkyl groups of the formula $C_nH_{2n}OH$, in which formula n indicates the numerals 2 or 3, are disclosed in German Auslegeschrift No. 25 04 724. These compounds are obtained by reacting amino alkane diphosphonic acids with cyclic ethers having preferably two to three carbon atoms in their ring nucleus, at increased temperature. When proceeding according to this process, only N-(hydroxy ethyl) or, respectively, N-(hydroxy propyl) derivatives of amino alkane diphosphonic acids are obtained.

German Auslegeschrift No. 22 11 578 discloses the use of amino lower alkane polyphosphonates and/or hydroxy alkane phosphonates in mixture with hydroxy or polyhydroxy compounds having two to six carbon atoms in their carbon chain and, if desired, with polyamino carboxylic acids, as stabilizing agents in bleaching baths. As has been demonstrated in the meantime, such combinations, used in place of silicates, have proved to have a very good stabilizing effect at higher temperatures and especially when bleaching is carried out according to the HT-process (high temperature process). These known stabilizing agents, however, do not yield satisfactory results when used for bleaching at low temperatures.

Furthermore, it is reported in the journal "Textilveredelung" Vol. 11 (1978), pages 159-160, in an article on "Investigations Regarding the Silicate-Free Stabilization of Peroxide-Containing Bleaching Liquors" that certain stabilizers yield satisfactory results. The composition of such stabilizers, however, is kept secret. Especially the stabilizer experiment mentioned in this report, is regarded as yielding satisfactory results, although, as is evident from the data given, a noticeable decrease of the DP-value from the initial value of 2,607 to a value of 2,373 is observed after a bleaching time of 24 hours.

SUMMARY OF THE INVENTION

It is therefore an object of the present invention to provide novel and advantageous N-(hydroxy methyl) amino alkane phosphonic acid compounds in which one or both hydrogen atoms, at the amino nitrogen atom, are replaced by the hydroxy methyl group.

Another object of the present invention is to provide a simple and advantageous process of producing such novel N-(hydroxy methyl) amino alkane phosphonic acid compounds.

A further object of the present invention is to provide compositions containing such N-(hydroxy methyl) amino alkane phosphonic acid compounds, these compositions being valuable and effective agents for stabilizing peroxide-containing bleaching baths for cellulose fiber materials.

Still another object of the present invention is to provide a highly effective method of bleaching cellulose fiber material which may contain synthetic fiber materials, by means of an alkaline bleaching bath containing such N-(hydroxy methyl) amino alkane phosphonic acid compounds.

In accomplishing the foregoing objects, there has been provided in accordance with one aspect of the present invention novel N-(hydroxy methyl)-1-amino alkane-1,1-diphosphonic acids and N,N-bis-(hydroxy methyl)-1-amino alkane-1,1-diphosphonic acids of the formula

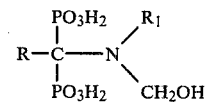

wherein
R indicates hydrogen or alkyl with one to three carbon atoms, and
$R_1$ indicaes hydrogen or hydroxy methyl ($-CH_2OH$).

In accordance with another aspect of the present invention, there has been provided a process for producing an N-(hydroxy methyl)-1-amino alkane-1,1-diphosphonic acid as defined above, comprising the steps of heating a 1-amino alkane-1,1-diphosphonic acid having 1 to 4 carbon atoms in the alkane group in an alkaline medium having a pH-value between about 8 and about 12 with from about 1 to 5 moles of formaldehyde at a temperature between about 60° C. and the boiling point of the reaction mixture, and isolating the resulting N-(hydroxy methyl)-1-amino alkane-1,1-diphosphonic acid from the reaction mixture.

In accordance with still another aspect of the present invention, there is provided a method for bleaching cellulose fibers and blends thereof with synthetic fibers, comprising the step of bleaching the fibers with an alkaline, peroxide-containing bleaching liquor, wherein the bleaching liquor contains as a peroxide stabilizing agent, between about 4% and about 30% of an N-(hydroxy methyl)-1-amino alkane-1,1-diphosphonic acid as defined above, this amount being calculated based on the content of 35% hydrogen peroxide present in the bleaching liquor. Also provided is an alkaline hydrogen peroxide-containing bleaching bath for bleaching cellulose fibers alone or blended with synthetic fibers, which contains, as a bleaching agent, an effective amount of hydrogen peroxide and, as a peroxide stabilizing agent, an N-(hydroxy methyl)-1-amino alkane-1,1-diphosphonic acid as defined above in an amount between about 4% and about 30% of the amount of 35% hydrogen peroxide present in the bleaching bath.

Further object, features and advantages of the present invention will become apparent from the detailed description of preferred embodiments which follow, when considered together with the attached figures of drawing.

BRIEF DESCRIPTION OF THE DRAWINGS

The attached drawings serve to illustrate the superior stabilizing effect of the N-(hydroxy methyl) amino alkane phosphonic acid compounds according to the present invention in comparison with known stabilizing agents and under varying conditions. In the drawings:

FIG. 1 illustrates the stabilizing effect depending upon the time the hydrogen peroxide solution is allowed to stand;

FIG. 2 illustrates the stabilizing effect upon hydrogen peroxide whereby ferric ions are added;

FIG. 3 shows the stabilizing effect of solutions to which sodium persulfate has been added;

FIG. 4 illustrates the stabilizing effect of solutions as in FIG. 3 but with the addition of ferric ions; and FIG. 5 illustrates the stabilizing effect in de-ionized water.

DETAILED DESCRIPTION OF PREFERRED EMBODIMENTS

The novel N-(hydroxy methyl) amino alkane phosphonic acid compounds of the above given formula are produced by reacting the corresponding 1-amino alkane-1,1-diphosphonic acids in an alkaline medium with one to five moles of formaldehyde at a pH-value between about 8 and about 12 at a temperature between about 60° C. and the boiling point of the reaction mixture. In order to isolate the reaction product, the resulting solution is treated with a strongly acid cation exchange agent, concentrated by evaporation, and caused to crystallize fractionally.

When proceeding as described hereinabove and using the corresponding 1-amino alkane-1,1-diphosphonic acids, there are obtained the following N-(hydroxy methyl)-1-amino alkane-1,1-diphosphonic acids, or N,N-Bis-(hydroxy-methyl)-1-amino alkane-1,1-diphosphonic acids:

| STARTING ACID | N-(HYDROXY METHYL)-1-AMINO ALKANE-1,1-DIPHOSPHONIC ACID |
|---|---|
| Amino methane diphosphonic acid | N-(hydroxy methyl) amino methane diphosphonic acid |
| Amino methane diphosphonic acid | N-N-Bis-(hydroxy methyl) amino methane diphosphonic acid |
| 1-Amino ethane-1,1-diphosphonic acid | N-(hydroxy methyl)-1-amino ethane-1,1-diphosphonic acid |
| 1-Amino ethane-1,1-diphosphonic acid | N,N-Bis-(hydroxy methyl)-1-amino ethane-1,1-diphosphonic acid |
| 1-Amino propane-1,1-diphosphonic acid | N-(hydroxy methyl)-1-amino propane-1,1-diphosphonic acid |
| 1-Amino propane-1,1-diphosphonic acid | N,N-Bis-(hydroxy methyl)-1-amino propane-1,1-diphosphonic acid |
| 1-Amino butane-1,1-diphosphonic acid | N-(hydroxy methyl)-1-amino butane-1,1-diphosphonic acid |
| 1-Amino butane-1,1-diphosphonic acid | N,N-Bis-(hydroxy methyl)-1-amino butane-1,1-diphosphonic acid |

The water-soluble salts of the novel N-(hydroxy methyl)-1-amino alkane-1,1-diphosphonic acids according to the present invention and especially the alkali metal salts can be produced by reacting the acids with alkali metal hydroxides or carbonates or with suitable organic bases. The alkaline reaction solutions obtained by reacting the alkaline amino alkane diphosphonic acid solutions with formaldehyde can be used directly as stabilizers without isolation of the salts.

The novel N-(hydroxy methyl)-1-amino alkane-1,1-diphosphonic acids, N,N-Bis-(hydroxy methyl)-1-amino alkane-1,1-diphosphonic acids and their water-soluble salts have proved to be excellent stabilizing agents, especially for peroxide-containing bleaching baths. Bleaching of cellulose fibers and especially of cotton, linen, nettle, and jute usually is effected with hydrogen peroxide or with compounds capable of splitting off hydrogen peroxide either in a long liquor (liquor ration 1:10–1:30), for instance, in a winch beck, or in a short liquor (liquor ratio 1:1–1:10) as it is used, for instance, in the impregnating process. The last-mentioned bleaching process can also be carried out as a so-called low temperature bleaching process. According to said process, the textile material impregnated with the bleaching liquor is kept on a batching roller or is placed on a trolley for a prolonged period of time.

In contrast to the phosphonic acid compounds disclosed in the above-mentioned German Auslegeschrift No. 22 11 578, the novel N-(hydroxy methyl) amino alkane phosphonic acids according to the present invention can also be used with excellent results in low temperature bleaching processes. It was found that the N-(hydroxy methyl)-1-amino alkane-1,1-diphosphonic acids or, respectively, the N,N-Bis-(hydroxy methyl)-1-amino alkane-1,1-diphosphonic acids according to the present invention exert such an excellent stabilizing effect that no decrease of the DP-values has been observed on bleaching cellulose fibers or blends thereof with other fibers for 24 hours. The DP-values even increased in many instances. The observed increase of the DP-values indicates that a better selective separation and removal of non-cellulosic and/or short chain cellulose material from the fiber is achieved.

The stabilizing effect of the N-(hydroxy methyl)-1-amino alkane-1,1-diphosphonic acids according to the present invention is so great that alkali metal gluconates and/or borates can be added in amounts up to about 90% without any disadvantageous effects. The possiblity of adding gluconates and/or borates is of considerable economic importance.

N,N-bis-(hydroxy methyl)-1-amino ethane-1,1-diphosphonic acid has proved to be especially useful and advantageous. This compound can be used alone or in mixture with the above-mentioned additives. Preferably, mixtures which contain about 40% to 50% of the phosphonic acid compounds of the present invention are used.

Excellent stabilizing effects are achieved by employing mixtures of the N-(hydroxy methyl) amino alkane phosphonic acids of the present invention with N,N-bis-(carboxy alkyl)-1-amino ethane-1,1-diphosphonic acids, the alkyl groups of which may contain up to three carbon atoms. Advantageously, the N-(hydroxy methyl) amino alkane phosphonic acid compound according to the present invention is used in mixture with carboxy alkyl phosphonic acid compounds in the proportion of about 1:1 to 2:1. It is quite surprising that such excellent results are achieved, since the N,N-bis-(carboxy alkyl)-1-amino ethane-1,1-diphosphonic acids, when used alone, are not very effective.

The preferred bleaching agent is hydrogen peroxide of a concentration of 35% or 50%. In its place there can also be used other compounds capable of splitting off oxygen.

The amount of stabilizer added to the bleaching bath should be between about 4% and about 30% and preferably is between 6% and 15%, calculated with respect to the amount of 35% hydrogen peroxide in the bleaching bath. Bleaching is effected in an alkaline medium at a pH-value between about 9 and about 14, so that, when using the free phosphonic acids, the corresponding salts are present in the bleaching bath. Of course, it is also possible to use the water-soluble salts and especially the alkali metal salts in place of the free acids.

A particular advantage of the present invention is to be seen in the feature that a stabilizer is made available for low temperature bleaching which stabilizer is superior, or at least equal, to the heretofore used silicate stabilizers, but which does not exhibit the disadvantages of the latter, such as the formation of deposits in the bleached material and in the bleaching apparatus. The degree of whiteness of fiber material bleached with the addition of the stabilizers according to the present invention is equal to that achieved when using silicates as stabilizers, while the ash content of the bleached goods is relatively low.

When carrying out the bleaching process with the stabilizers according to the present invention, wetting agents can be added in order to shorten the wetting time. For this purpose, any conventional wetting agent can be used provided it is stable and effective in an alkaline medium and is compatible with the phosphonic acids and all the components of the stabilizer composition. Suitable wetting agents are the anion-active and the non-ionic wetting agents as well as mixtures thereof. Preferred anion-active wetting agents are, for instance, the alkyl aryl sulfonates, fatty acid condensation products, protein degradation products, and others, as well as their salts. Non-ionic wetting agents which can be used are, for instance, adducts of ethylene oxide to fatty alcohols, fatty acid amides, alkyl phenols, and others.

The following examples serve to illustrate the present invention without, however, limiting the same thereto. Examples 1 to 5 describe more in detail the process of producing the novel N-(hydroxy methyl)-1-amino alkane-1,1-diphosphonic acids according to the present invention.

EXAMPLE 1

In order to produce N-(hydroxy methyl)-1-amino ethane-1,1-diphosphonic acid, there are dissolved 102.5 g of 1-amino ethane-1,1-diphosphonic acid in 280 g of a 30% potassium hydroxide solution, while stirring. 100 g of a 30% fomaldehyde solution are added to the resulting solution. The reaction mixture is boiled under reflux for 3 hours. The resulting solution is treated with a strongly acidic cation exchange agent, concentrated by evaporation, and fractionally crystallized. The yield of N-(hydroxy methyl)-1-amino ethane-1,1-diphosphonic acid is about 70%.

Analysis: Calculated 15.33% C; 5.96% N; 26.35% P. Found: 15.8% C; 5.8% N; 25.9% P.

Ratio of C:N:P = 3.2:1:2.0.

EXAMPLE 2

In order to produce N,N-bis-(hydroxy methyl)-1-amino ethane-1,1-diphosphonic acid, there are introduced 205 g of 1-amino ethane-1,1-diphosphonic acid into a solution of 168 g of potassium hydroxide in 300 g of distilled water. The mixture is heated to 80° C. 300 g of a 30% fomaldehyde solution are added drop by drop thereto at said temperature. Thereafter, the resulting reaction solution is worked up in the same manner as described hereinabove in Example 1. N,N-1-bis-(hydroxy methyl)-1-amino ethane-1,1-diphosphonic acid is obtained in a yield of 85%.

Analysis: Calculated: 19.28% C; 5.62% N; 24.86% P. Found: 19.1% C; 5.5% N; 24.9% P.

Ratio of C:N:P = 4.0:1:2.0.

EXAMPLE 3

N,N-bis-(hydroxy methyl) amino methane diphosphonic acid is produced by proceeding as described in Example 1 by reacting 38.2 g of amino methane diphosphonic acid which are stirred in 100 ml. of water. The mixture is adjusted to a pH-value of 10.0 by the addition of potassium hydroxide solution. The resulting solution is reacted with 40 g of a 37.5% formaldehyde solution at 90° C. and the N,N-bis-(hydroxy methyl) amino methane diphosphonic acid is isolated from the reaction mixture as described hereinabove.

EXAMPLE 4

In the same manner there can be prepared an about 29% solution of the trisodium salt of N,N-bis-(hydroxy methyl)-1-amino propane-1,1-diphosphonic acid by dissolving 109.5 g of 1-amino propane-1,1-diphosphonic acid in 246 ml. of a 20% sodium hydroxide solution, adding drop by drop thereto 150 g of a 30% formaldehyde solution at 80° C., and keeping the reaction mixture at said temperature for 3 hours.

EXAMPLE 5

A reaction product consisting of about 25% to 30% of N-(hydroxy methyl)-1-amino ethane-1,1-diphosphonic acid and about 70% to 75% of N,N-bis-(hydroxy methyl)-1-amino ethane-1,1-diphosphonic acid is obtained by dissolving 264 kg of 1-amino ethane-1,1-diphosphonic acid in 440 of a 50% potassium hydroxide solution in a one cubic meter reaction vessel of special alloyed steel (stainless steel) provided with a stirrer, heating the solution to 70° C., and adding thereto at said temperature 322 kg of a 30% formaldehyde solution at a speed of addition of 130 l. per hour. The resulting reaction mixture is then heated at 100° C. for 3 hours in order to complete the reaction.

In a similar manner there can be obtained other N-(hydroxy methyl)-1-amino alkane-1,1-diphosphonic acids and N,N-bis-(hydroxy methyl)-1-amino alkane-1,1-diphosphonic acids, or mixtures thereof, of their water-soluble salts.

In order to determine the stabilizing effect and also the bleaching effect of the novel N-(hydroxy methyl)-1-amino alkane-1,1-diphosphonic acids of the present invention, the following experiments are carried out:

EXAMPLE 6

Stabilizing Effect on Hydrogen Peroxide in Concentrated Bleaching Liquors

Stabilizing bleaching liquors of the following composition are prepared:

6 ml./l. of stabilizer,
25 ml./l. of 50% sodium hydroxide solution,
5 g./l. of wetting agent (mixture of anionic and non-ionic surfactants),
50 ml./l. of 35% hydrogen peroxide.

The content of active oxygen of said solution is determined by titration with potassium permanganate after allowing the solution to stand for 2, 4, 6, 16, 40, 64 and 140 hours. The bleaching solutions are prepared with water of 12° German hardness.

Another test is carried out with distilled water in order to exclude any possible influence of the hardness causing agents upon the stabilizer.

In the following experiments, a threefold concentrated bleaching bath is used, as it is conventionally employed for bleaching of wet fiber goods. Additionally, the tests are supplemented by adding to the composition of Example 6 5 g/l. of sodium persulfate and, furthermore, by carrying out each test with or without the addition of 5 mg/l. of ferric ions. In those tests in which waterglass is used as stabilizer, 20 ml/l. of waterglass is added.

The following stabilizer compositions are prepared and used in the stabilizing tests by adding the respective amounts to the bleaching liquor of Example 6.

EXAMPLE 7

Stabilizer composition K 1 consists of:

40 parts by weight of N,N-bis-(hydroxy methyl)-1-amino ethane-1,1-diphosphonic acid,
45 parts by weight of a 40% potassium gluconate solution,
5 parts by weight of boric acid, and
10 parts by weight of a 50% potassium hydroxide solution.

EXAMPLE 8

Stabilizer composition K 2 consists of:
30 parts by weight of N,N-bis-(hydroxy methyl)-1-amino ethane-1,1-diphosphonic acid,
15 parts by weight of N,N-bis-(carboxy methyl)-1-amino ethane-1,1-diphosphonic acid,
40 parts by weight of a 40% potassium gluconate solution,
5 parts by weight of boric acid, and
10 parts by weight of a 50% potassium hydroxide solution.

In order to compare the stabilizing effect of the phosphonic acids according to the present invention with that of the compounds disclosed in the above-mentioned German Auslegeschrift No. 22 11 578, the following composition according to that application is prepared:

EXAMPLE 9

(Comparative)

Stabilizer Composition V 1 consists of:

32 parts by weight of diethylene triamino pentamethylene phosphonic acid,
18 parts by weight of diethylene triamino pentaacetic acid, and
50 parts by weight of a 40% potassium gluconate solution.

The heretofore used stabilizing waterglass solution mentioned above is designated as Composition V 2 (Comparative).

The stabilizing effects observed by using the compositions according to Examples 6 to 9 and the waterglass solution V 2 are shown in the diagrams of FIGS. 1 to 5.

FIG. 1 (without the addition of sodium persulfate and/or ferric ions) shows the excellent stabilizing effect of the compositions K 1 and K 2 (Examples 7 and 8). The waterglass stabilizer V 2 which, heretofore, was regarded as unsurpassed in its activity, is unquestionably inferior. The stabilizer V 1 (Example 9) shows the worst effect under the conditions of the comparative test.

FIG. 2 (with the addition of ferric ions) shows that the catalytic action of ferric ions is almost completely eliminated by the stabilizing compositions K 1 and K 2 (Examples 7 and 8), but is still noticeable when using the waterglass composition V 2, even if increased amounts of said stabilizer are used. Remarkable and unexplainable is the considerable decrease in activity observed at the beginning of the test with composition V 1 (Example 9), while subsequently no further substantial loss in active oxygen takes place.

FIG. 3 illustrates the results obtained with the various stabilizer compositions, when sodium persulfate is added. It is also evident from the curves that no substantial change in the active oxygen content takes place by the addition of persulfate to the bleaching baths containing the stabilizer compositions K 1 and K 2 according to the present invention. In contrast thereto, the bleaching bath containing waterglass as stabilizer, i.e., the stabilizer composition V 2, shows a surprisingly great loss of active oxygen, especially when using lower concentrations of the waterglass stabilizer. The bleaching bath to which the stabilizing composition V 1 (Example 9) is added, shows a stabilizing effect similar to that observed without the addition of persulfate.

FIG. 4 illustrates the results achived when sodium persulfate and ferric ions are added to the bleaching bath. All the curves clearly show that persulfate and ferric ions, when present in the bath at the time, catalytically affect to a considerable extent the decomposition of hydrogen peroxide. When increasing to 16% the concentration of the stabilizer which in the preceding tests amounts to 12% of the added milliliter amount of 35% hydrogen peroxide, there is obtained by means of the compositions K 1 and K 2 a stabilizing effect corresponding to that shown in FIG. 1, i.e., the active oxygen is retained in the bath almost without any loss.

When using distilled water in place of water of 12° German hardness, the stabilizing effect of the compositions K 1, K 2, V 1, and V 2 can be seen from the curves of FIG. 5. The decrease in active oxygen in the bleaching bath to which the stabilizer composition V 1 (Example 9) has been added, is quite considerable. In contrast thereto, substantially no loss in active oxygen is observed when adding the stabilizer compositions K 1 and K 2 (Examples 7 and 8) to the bleaching bath. Even still greater is the decrease in active oxygen, when adding the stabilizer composition V 2 (waterglass) to the bleaching bath. In this case, there is no difference between varying amounts of stabilizer V 2 added to the bleaching bath.

These results clearly show that the stabilizing effect of any of the agents tested as stabilizers for hydrogen peroxide is certainly not due to its sequestering power, because distilled water does not contain any heavy metal ions which cause catalytic decomposition of hydrogen peroxide. On the other hand, it is evident that the stabilizing action of waterglass is achieved only in combination with alkaline earth metal ions.

EXAMPLE 10

Determination of the Bleaching Effect Depending Upon the Bleaching Time, when Proceeding According to the Low Temperature Bleaching Process 1. Material used in the test: Sized cotton fabric.

Degree of whiteness: 59.1
DP-degree: 1970

2. Composition of the bleaching liquor:

6 ml./l. of stabilizer,
25 ml./l. of 50% sodium hydroxide solution,
5 g./l. of wetting agent,
5 g./l. of sodium persulfate, and
50 ml./l. of 35% hydrogen peroxide.

The bleaching bath is varied in its composition by adding thereto
3 ml./l. of waterglass. The term waterglass refers to an aqueous solution of sodium silicate having the following characteristics:

| SPECIFIC GRAVITY | CONCENTRATION | Na$_2$O ca. | SiO$_2$ ca. | H$_2$O ca. | DRY MATTER ca. | WT RATIO Na$_2$O:SiO$_2$ ca. | MOLE RATIO Na$_2$O:SiO$_2$ ca. |
|---|---|---|---|---|---|---|---|
| 1.34–1.38 | 37–40° B'e | 8.15% | 27.2% | 64.65% | 35.35% | 1:3.3 | 3.4 |

3. Conditions under which the test is carried out:

Impregnation: Dry/wet with 100% squeezing-out effect.
Bleaching time: 2, 4, 6, and 24 hours.
Water used: Water of 12° German hardness.
Rinsing: Hot; cold; cold with 1% acetic acid.
Temperature: Room temperature 4. Test results:

| STABILIZER | DEGREE OF WHITNESS (REMISSION AFTER HOURS) | | | | DP-VALUE AFTER HOURS |
|---|---|---|---|---|---|
| | 2 | 4 | 6 | 24 | 24 |
| K 1 | 77.8 | 80.3 | 81.5 | 83.0 | 2.130 |
| K 2 | 77.6 | 80.0 | 81.2 | 83.0 | 2.100 |
| V 1 | 77.4 | 79.6 | 80.2 | 82.5 | 2.100 |
| V 2 (Waterglass 6 ml./l.) | 77.7 | 79.8 | 80.0 | 83.0 | 1.900 |
| V 2 (Waterglass 20 ml./l.) | 77.9 | 80.5 | 81.1 | 83.5 | 2.100 |
| K 1 + 3 ml. waterglass | 77.8 | 80.3 | 81.5 | 83.6 | 2.100 |
| K 2 + 3 ml. waterglass | 78.4 | 80.4 | 81.7 | 83.6 | 2.100 |
| V 1 + 3 ml. waterglass | 78.1 | 79.8 | 80.5 | 83.0 | 2.060 |

As is evident from the tests as described hereinabove and illustrated in the drawings, the stabilizer K 1 and K 2 of the present invention are superior to the known stabilizer V 1 in their bleaching effect as well as in the DP-value of the bleached cellulose material. With respect to waterglass (V 2), the stabilizer K 1 and K 2 are to be considered as being at least equal thereto. Combinations of the stabilizers K 1 and K 2 with waterglass do not yield any noticeable changes and improvements. The determined DP-value of the stabilizers K 1 and K 2 with the addition of waterglass are very similar to those determined without the addition of waterglass.

Of course, many changes and variations in carrying out the process of producing the novel N-(hydroxy methyl) amino alkane phosphonic acids according to the present invention, in the reaction conditions, such as duration, reaction temperature, and concentration of the reactants, and the like, as well as in the composition of the stabilizer additives added to the peroxide-containing bleaching liquors, and in the bleaching process may be made by those skilled in the art in accordance with the principles set forth herein.

What is claimed is:

1. An N-(hydroxy methyl)-1-amino alkane-1,1-diphosphonic acid or an N,N-Bis-(hydroxy methyl)-1-amino alkane-1,1-diphosphonic acid of the formula

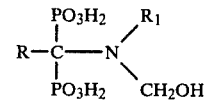

wherein
R indicates methyl, and
R$_1$ indicates hydrogen or the hydroxy methyl group (—CH$_2$OH), and the water-soluble salts of said acid.

2. A phosphonic acid according to claim 1, in which R is methyl and
R$_1$ is hydrogen, said acid being N-(hydroxy methyl)-1-amino ethane-1,1-diphosphonic acid.

3. A phosphonic acid according to claim 1, in which R is methyl and
R$_1$ is the hydroxy methyl group, said acid being N,N-Bis-(hydroxy methyl)-1-amino ethane-1,1-diphosphonic acid.

* * * * *